United States Patent
Chang et al.

(10) Patent No.: US 6,787,013 B2
(45) Date of Patent: Sep. 7, 2004

(54) BIOSENSOR

(75) Inventors: Ching-Yu Chang, Pingtung Hsien (TW); Cherng-Jyh Lee, Hsinchu (TW); Tzer-Ming Chen, Taipei (TW)

(73) Assignee: Eumed Biotechnology Co., Ltd., Taipei Hsien (TW)

( * ) Notice: Subject to any disclaimer, the term of this patent is extended or adjusted under 35 U.S.C. 154(b) by 365 days.

(21) Appl. No.: 09/949,693

(22) Filed: Sep. 10, 2001

(65) Prior Publication Data

US 2003/0046811 A1 Mar. 13, 2003

(51) Int. Cl.$^7$ .............................................. G01N 27/26
(52) U.S. Cl. .................. 204/412; 204/294; 204/403.14; 29/825; 29/830; 29/846; 29/847
(58) Field of Search .......................... 29/825, 830, 846, 29/847; 204/294, 403.14, 412

(56) References Cited

U.S. PATENT DOCUMENTS

| | | | |
|---|---|---|---|
| 4,654,127 A | * 3/1987 | Baker et al. ................. 205/792 |
| 5,120,420 A | 6/1992 | Nankai et al. | |
| 5,200,706 A | * 4/1993 | Yada ........................... 324/446 |
| 5,288,636 A | 2/1994 | Pollmann et al. | |
| 5,437,999 A | 8/1995 | Diebold et al. | |
| 5,575,895 A | 11/1996 | Ikeda et al. | |
| 5,650,062 A | * 7/1997 | Ikeda et al. .................. 205/778 |
| 5,651,869 A | 7/1997 | Yoshioka et al. | |
| 5,770,439 A | 6/1998 | Bilitewski et al. | |
| 5,795,364 A | 8/1998 | Payne et al. | |
| 5,798,030 A | 8/1998 | Raguse et al. | |
| 5,798,031 A | 8/1998 | Charlton et al. | |
| 5,866,353 A | 2/1999 | Berneth et al. | |
| 6,004,441 A | 12/1999 | Fujiwara et al. | |
| 6,027,944 A | 2/2000 | Robinson et al. | |
| 6,488,828 B1 | * 12/2002 | Bhullar et al. ......... 204/403.01 |
| 6,541,216 B1 | * 4/2003 | Wilsey et al. ................. 435/26 |
| 6,662,439 B1 | * 12/2003 | Bhullar ........................ 29/825 |

* cited by examiner

Primary Examiner—Rick Kiltae Chang
(74) Attorney, Agent, or Firm—William E. Pelton, Esq.

(57) ABSTRACT

A spacer forming method for a biosensor that has a biosensor possessing a capillary sampling channel and electrical connecting tracks for the use of a specific portable meter. A pair of electrodes is printed on an insulating base plate to be the transducer of the electrochemical biosensor by means of the screen-printing technology. The advanced thick-film printing technology is employed to construct the spacer component of the sampling channel that precisely controls the volume of a sample solution. Therefore, the spacer forming method reduces the usage of adhesive that otherwise causes a serious problem during a continuous punching procedure. Furthermore, the embedded switch pad on the biosensor is introduced to be instead of a micro switch in a connector of the portable meter.

10 Claims, 6 Drawing Sheets

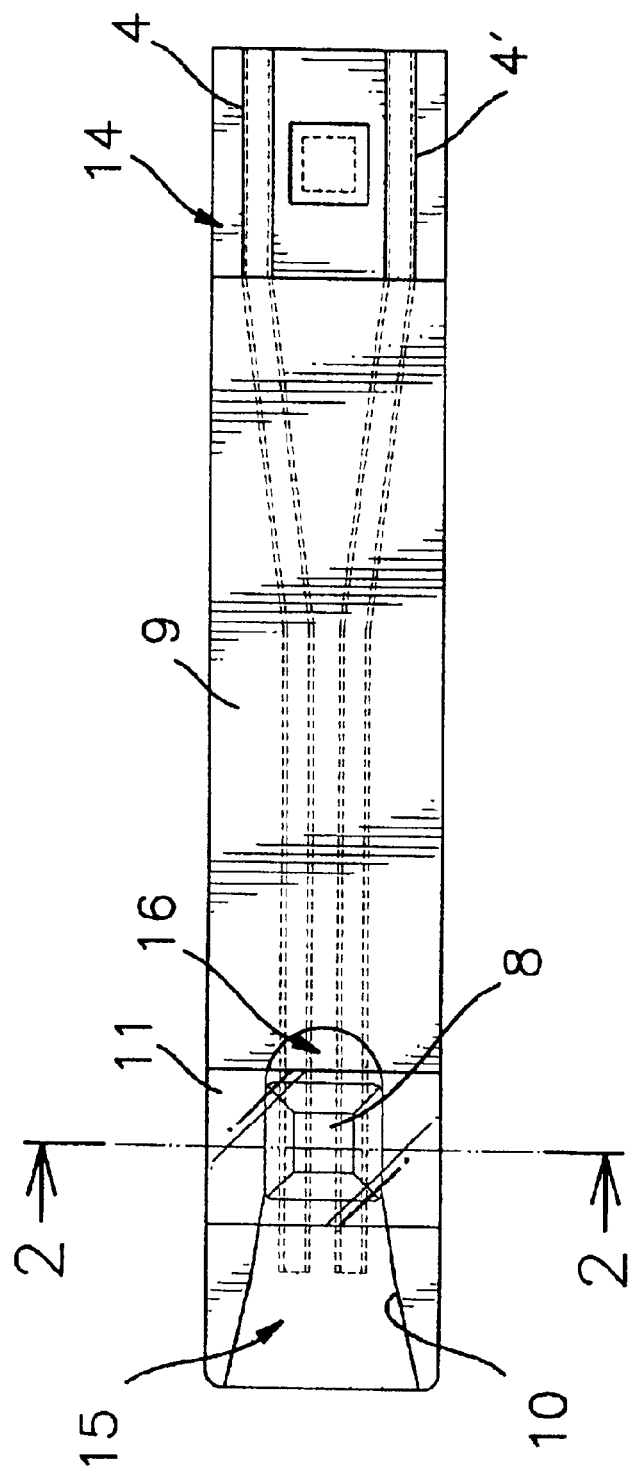

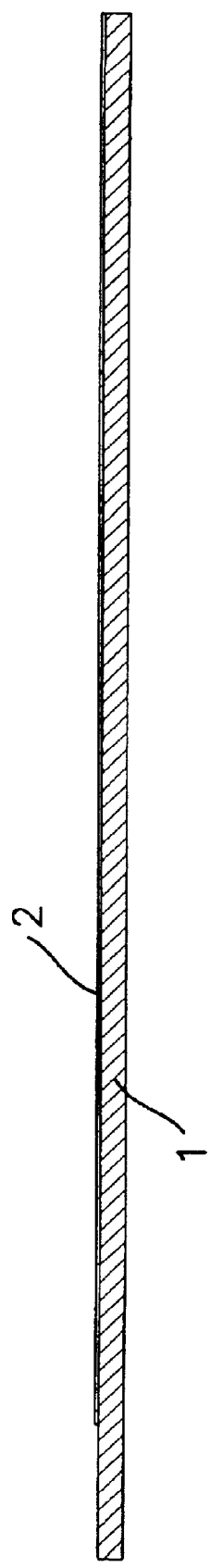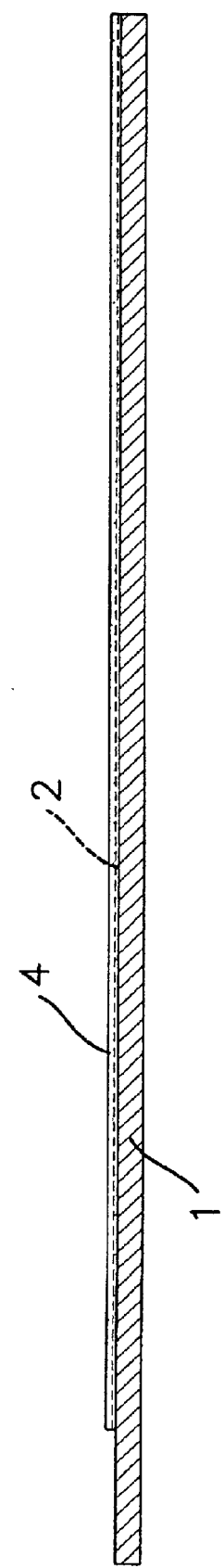

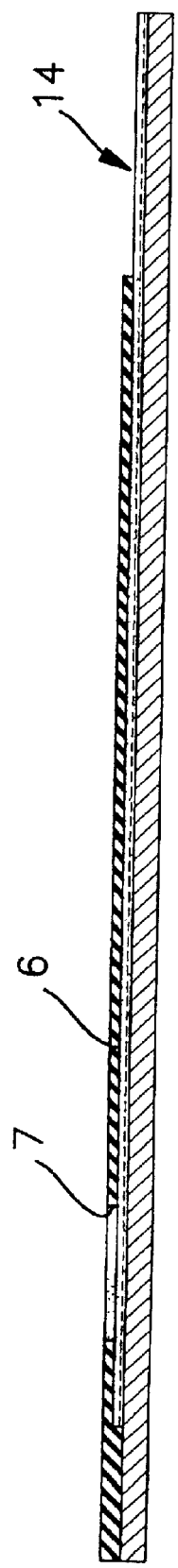
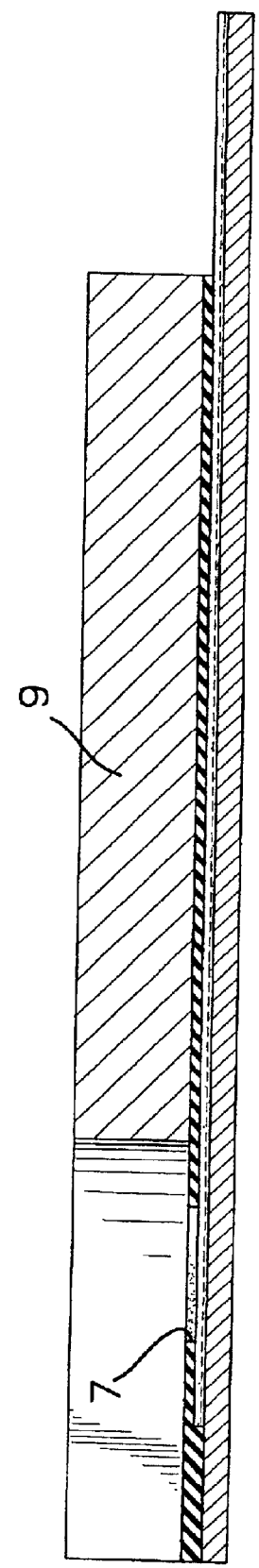

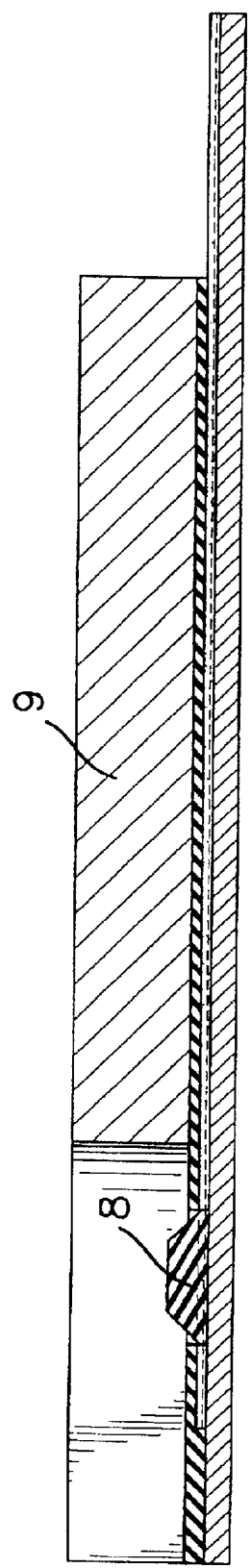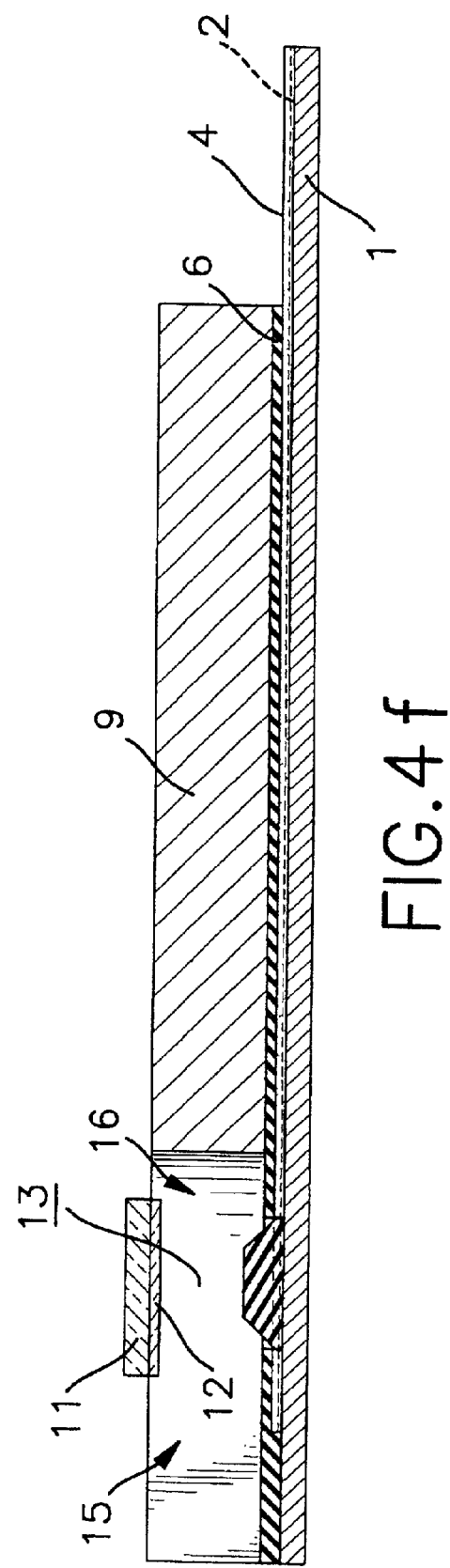

BIOSENSOR

BACKGROUND OF THE INVENTION

1. Field of the Invention

The present invention relates to a spacer forming method used for a biosensor, and more particularly a biosensor having a spacer constructed by thick-film printing technology. The present invention also relates to the structure of the biosensor that is made in accordance with this spacer forming method.

2. Description of Related Art

Several disposable biosensors were developed to determine the different substances in the human body fluid. Especially, the glucose strip is the best application example of the disposable biosensor, and this product has become an important medical device for the diabetics to monitor their blood glucose away from hospital. To monitor the glucose levels frequently is a fact of everyday life for diabetic individuals, and a number of glucose meters are now available which permit the individual to test the glucose level in a small amount of blood.

For the convenience of applying a blood sample and using small amount of blood, it is useful to use the capillary sampling method to quantitatively introduce the very small amount of sample into a reaction area. The construction of capillary sample channel needs a spacer component to provide the wall of the sample channel, and the adhesion of a sheet with a specific thickness on the biosensor is the most popular method found in the conventionally commercial strip. Examples of device of this type were disclosed in U.S. Pat. No. 5,120,420; U.S. Pat. No. 5,288,636; and U.S. Pat. No. 5,437,999 which are incorporated herein by reference.

The conventional biosensor is usually constructed by adhering the spacer component onto the base plate in a position relative to the electrode. However, the use of this method to constrict the spacer component causes a serious problem in the punching process because a glue sheet is adhered to the mold and this affects the precision of punching element, and slows down the throughput.

Additionally, in the general electrochemical glucose meter, a micro switch is embedded in the connector. An expensive and complex connector has to be developed but the connectors can't identify whether the inserted strip is up side or not. Furthermore, the micro switch is usually used to be a trigger switch instead of the power switch, and the battery power still supplies the static current to the circuits when the strip is withdrawn from the meter. Therefore, the connecting of micro switch does not shut down the meter completely, and the extra power consumption occurs when the meter is idle. According to the above description, the conventional biosensors still have drawbacks and thus there is need for an improved biosensor.

The present invention has arisen to mitigate and/or obviate the disadvantages of the conventional biosensor.

SUMMARY OF THE INVENTION

A first objective of the present invention is to provide a spacer forming method used for a biosensor to make the manufacturing process for the biosensor effective. By means of stainless stencil printing technology, a spacer layer is constructed to be the wall of the sampling channel and a sample application port is controlled by adjusting the thickness of the printed pattern.

A second objective of the present invention is to provide a spacer forming method used for a biosensor, wherein the biosensor reduces sample demands and introduces a sample reagent into a reaction layer precisely and rapidly by the capillary sampling channel.

A third objective of the present invention is to provide a spacer forming method used for a biosensor, wherein the biosensor eliminates several adhering steps by constructing a uniform spacer layer so as to simplify the production process and meet the requirement of accuracy.

A fourth objective of the present invention is to provide a spacer forming method used for a biosensor, wherein an actuating strip is printed on the same side of electrodes on the biosensor so as to control the electric states of the biosensor.

Further benefits and advantages of the present invention will become apparent after a careful reading of the detailed description with appropriate reference to the accompanying drawings.

BRIEF DESCRIPTION OF THE DRAWINGS

FIG. 3 is a top view of the biosensor in assembly in accordance with FIG. 2;

FIGS. 4a–4f are schematically side sectional views of a process for manufacturing the biosensor in accordance with the present invention.

DETAILED DESCRIPTION OF THE INVENTION

In this invention, a screen-printing technology is applied to form electrode and insulating patterns on a supporting sheet, but not to a spacer layer. The traditional screen-printing technology prints the pattern with a thickness about several tens of micrometers. However, with the use of a stainless stencil and some specific paste, a much thicker and finer pattern than other patterns can be achieved. The stainless stencil printing provides a potential application for the biosensor industry as disclosed in this invention.

Figure 1:
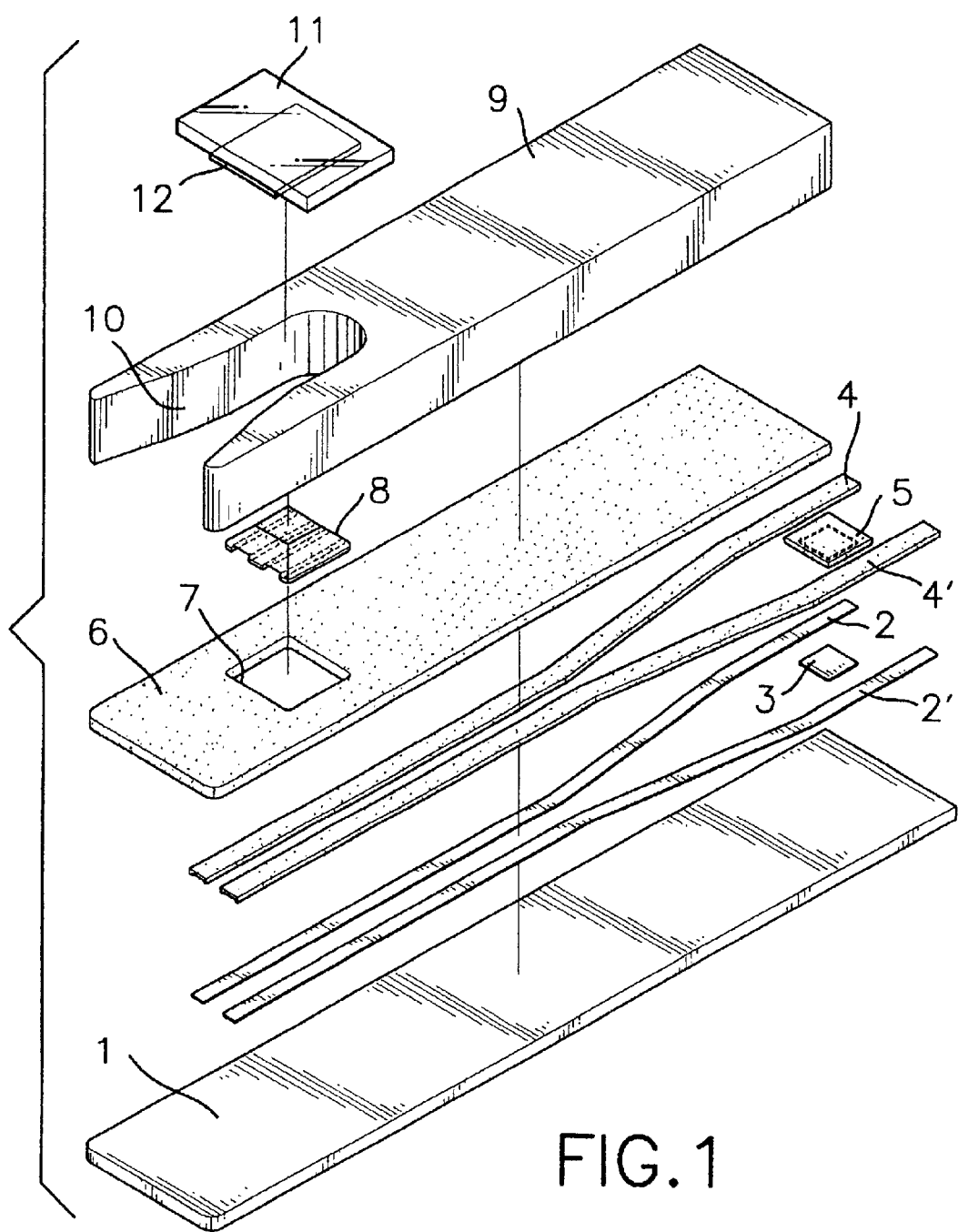
FIG. 1 is an exploded perspective view of a biosensor as an embodiment in accordance with the present invention.

With reference to FIGS. 1 and 3, a spacer forming method used for a biosensor is disclosed wherein the biosensor is composed of a substrate (1), an anode conducting track (2) and a cathode conducting track (2'), a pair of electrode tracks (4, 4'), a switch, an insulating layer (6), a reagent layer (8), an insulating spacer layer (9), and a protecting layer (11).

The flattened substrate (1) possessing the properties of electrical insulation, thermal resistance, as well as a required surface flatness is selected to be a support of the biosensor. The electrical insulating property allows the construction of the two independent conducting tracks (2, 2') to be secured on the substrate (1), and the thermal resistance and surface flatness requirements reduce problems in the manufacturing process. The preferred thermal resistance property is that the substrate (1) shows no obvious deformation from 40° C. to 200° C. which occur in a thermal curing process of the screen-printing paste. Materials of the substrate (1) are selected, but not limited, from following groups: polyvinyl chloride (PVC), polyethylene terephthalate (PET), polycarbonate (PC), polypropylene (PP), polyethylene (PE), polybutylene terephthalate (PBT), polystyrene (PVDF), polyamide (PA), bakelite, fiberglass, glass, ceramics etc.

The anode conducting track (2) and cathode conducting track (2') are printed on the substrate (1) by the means of screen-printing or stainless stencil printing technology. The materials of the anode conducting track (2) and the cathode conducting track (2') are selected, but not limited to, from following groups: carbon paste, silver paste, silver chloride paste, gold paste, palladium paste, gold, platinum, and palladium.

The electrode tracks (4,4') are disposed on the corresponding conducting track (2,2') and provide a suitable surface for electrochemical measurement of the biosensor. The materials of the electrode tracks (4,4') are selected from, but not limited to, from following group: carbon paste, gold paste, palladium paste, gold, platinum, and palladium.

The switch is composed of a conducting pad (3) and a switch pad (5) and turns on the electrical system when the biosensor is inserted into a connector of a meter. The switch pad (5) is constructed on the conducting pad (3) that is mounted on the connecting area (14) and the switch pad (5) will connect at least two pins of the connector when strip is inserted. The conducting pad (3) is made of the same material with the conducting tracks (2, 2') and the switch pad (5) is made of the same material with the electrode tracks (4,4').

The insulating layer (6) has an opening defined therein to construct a reaction area (7). The reaction area (7) includes the electrode tracks (4,4') and defines the electrode area by the opening. A connecting area (14) (see FIG. 3) is disposed in the insulating substrate (1) to electrically connect with the meter. Material of the insulating layer (6) is selected from, but not limited to, the following group: acrylic resin, epoxy resin, polyurethane resin, silicon resin, phenol resin, alkyd resin, maleic alkyd resin, urea resin, polyester resin etc.

The insulating spacer layer (9) is disposed on the insulating layer (6) and a sample ditch (10) is reserved on the spacer layer (9). The sample ditch (10) is at a position corresponding to the reaction area (7) and constructs walls of the reaction area (7) to block a sample solution inside. The thickness of the spacer layer (9) is 0.1–0.4 mm and the material of the spacer layer (9) is selected from, but not limited to, the following group: acrylic resin, epoxy resin, polyurethane resin, silicon resin, phenol resin, alkyd resin, maleic alkyd resin, urea resin, polyester resin etc.

The reagent layer (8) is disposed on the reaction area (7) and re-dissolved rapidly when the reagent layer (8) contacts with the sample solution. The components of the reagent layer are enzyme, buffer solution, carrier, electrical mediator, and surfactant.

The protecting layer (11) is transversely mounted on the sample ditch (10) of the spacer layer (9) to form an inlet port (15) and an outlet port (16) (see FIG. 3). A hydrophilic membrane is adhered on a face directed toward to the reaction area (7) of the biosensor. Material of the hydrophilic membrane is selected from at least one of the following group: Triton X-100, polyoxymethylene sorbitan, starch, carboxymethyl cellulose, gelatin, acrylate, polyethylene glycol, polyvinyl alcohol, and polyvinylpyrrolidone.

Figure 2:
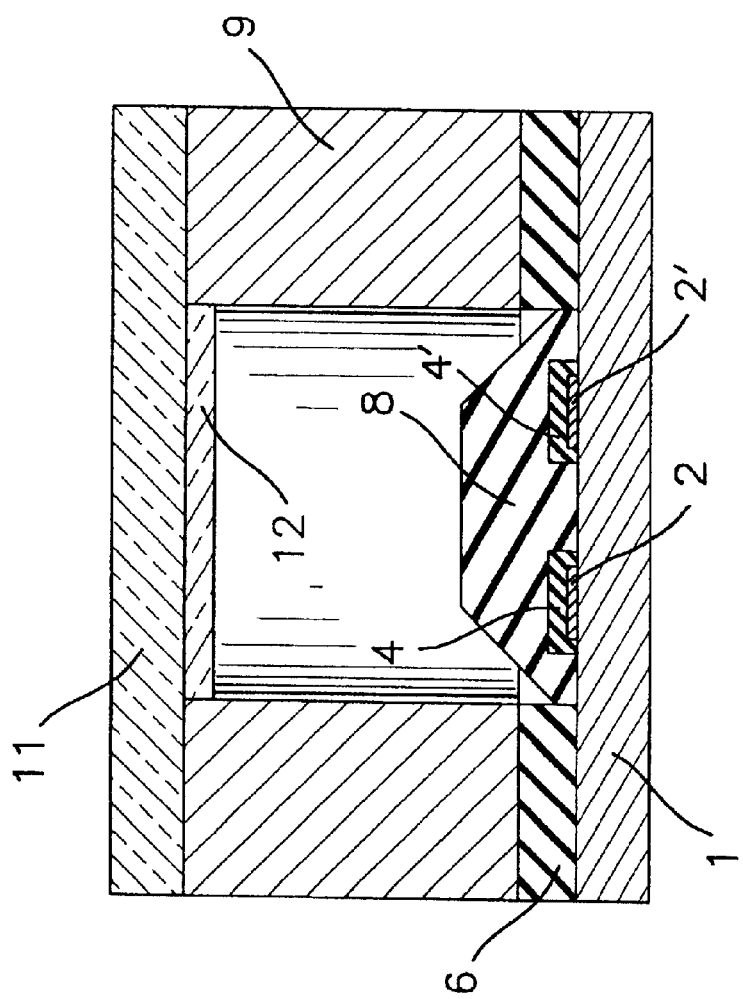
FIG. 2 is a front-side sectional view of the biosensor along line 2—2 in accordance with FIG. 3.

Now referring to FIGS. 2 and 3, the protecting layer (11) adhered on the spacer layer (9) reserves the inlet (15) and the outlet (16) and constructs a sampling channel (13) with the spacer layer (9) as a wall. The protecting layer (11) is a base to provide protection such that the following packaging process in manufacture and user's touch do not cause the damage of the reagent layer (8). Furthermore, an inner side of the protecting layer (11) is coated with the hydrophilic membrane (12) that enhances the capillary force of the sampling channel (13) and accelerates the flow of the sample solution in the sampling channel (13).

The spacer forming method for manufacturing the biosensor is illustrated in detail as following steps in accompaniment with FIGS. 4a–4f.

Step 1 (as Shown in FIG. 4a)

Multiple pairs of the anode conducting track (2) and the cathode conducting track (2'), and the conducting pad (3) are printed on the substrate (1) by means of the screen-printing or stainless stencil printing technology, and the solvent of the paste is evaporated by heating the matter in an oven as the requirements of the selected paste. The preferred conducting layer is made of the screen printable silver paste.

Step 2 (as Shown in FIG. 4b)

Multiple pairs of electrode tracks (4,4') and the switch pad (5) are disposed and overlapped respectively on the corresponding conducting tracks (2,2') and the conducting pads (3) of the conducting layer by means of screen-printing or stainless stencil printing technology. The solvent of the electrode tracks (4,4') and the switch pad (5) are dried by heating in an oven as the requirements of the selected paste. The preferred conducting layer is made of the screen printable carbon paste.

Step 3 (as Shown in FIG. 4c)

A plural set of insulating layers (6) is disposed in the electrode tracks (4,4') and the switch pad (5) by screen-printing or stainless stencil printing technology again, and the plural set of insulating layers is cured as the requirements of the selected paste to solidify the printed pattern. Each insulating layer (6) has the opening reserved for the ingredient application in the reaction area (7) and the connecting area (14) reserved for electrical signal transmission with the meter.

Step 4 (as Shown in FIG. 4d)

A plural set of spacer layers (9) with a thickness of about 0.1–0.4 mm is disposed on the insulating layer (6) by the stainless stencil printing technology, and then cured as the requirements of the selected paste to solidify the printed pattern. The sample ditch (10) is reserved in each spacer layer (9) to construct the wall of the sampling channel (13), so the sample volume of this biosensor is controlled by the thickness of the spacer layer (9).

Step 5 (as Shown in FIG. 4e)

An ingredient solution is quantitatively dropped on the plural set of the reaction area (7) and dried at a temperature range of 40° C. to 50° C. to form the plural set of reagent layers (8).

Step 6 (as Shown in FIG. 4f)

A roll of transparent foil with one side coated with the hydrophilic membrane is adhered to the insulating spacer layer (9) to form the protecting layer (11) so as to construct the sampling channel (13) with the spacer layer (9) and the insulating layer (6). With the part coverage of the protecting layer (11) on the sample ditch (10), the inlet port (15) and the outlet port (16) are reserved respectively on the ends of the sample ditch (10).

Step 7 (not Shown)

Cutting the individual biosensor from the substrate (1) by means of a punching process.

The present invention is described in detail in accordance with the following embodiments.

EXAMPLE 1

A conducting film of silver paste is screen printed on a flat surface of a PET sheet functioning as the electrically insulating substrate (1) to form the anode conducting track (2) and the cathode conducting track (2') and the conducting pad (3). The silver paste is dried at a temperature of 130° C. for 30 min. Then, a carbon paste is printed on the conducting film to overlap the anode conducting track (2), the cathode conducting track (2'), and the conducting pad (3) respectively, to form the anode electrode track (4), the cathode electrode track (4') and the switch pad (5), and the carbon paste is dried at a temperature of 130° C. for 30 min.

Next, a layer of insulating paste is printed on the electrode layer (4,4', and 5) and cured with the polymer by the irradiation of UV light to form the insulating layer. The reaction area (7) defines the geometry area of partial electrode tracks (4,4') and restricts the ingredient solution in a defined region to avoid the flow problem of the ingredient solution during applying process. The connecting area (14) includes partial electrode tracks (4,4') and the switch pad (5). Hereafter, a thick layer of polyurethane polymer film is disposed by the use of stainless stencil screen-printing technology on the insulating layer (6) and is cured under the irradiation of UV light to form the spacer layer (9). Additionally, the sample ditch (10) is reserved at one end of the spacer layer (9).

Then, a composition of the following formula is dropped on the surface of the reaction area (7) and dried at a temperature of 50° C. for 15 min to form a reagent layer (8).

| | |
|---|---|
| Glucose oxidase | 0.6% |
| PVA | 1.0% |
| Potassium ferricyanide | 6.0% |
| Phosphate buffer | 92.4% |
| Triton X-100 | 0.5% |

Next, the protecting layer (11) coated with surfactant is adhered to the spacer layer (9) and partly covers the sample ditch (10) to form the sampling channel (13). The exposed openings of the sample ditch (10) form the inlet port (15) and the outlet port (16) spontaneously. Finally, the plurality of biosensors is punched from the substrate (1) to produce individual versions.

The process of constituting the spacer layer (9) is simplified by the use of the stainless stencil screen-printing technology so as to constitute an accurate sampling channel (13). Furthermore, the evaporation of the sample solution is minimized during the measurement thereby having a measurement of high accuracy. The transparent property of the protecting layer (11) enables users to easily determine whether the sample channel (13) is filled or not when they are introducing their sample solution.

As soon as the sample solution contacts with the inlet port (15), the sample solution is introduced into the sampling channel (13) and stopped at the outlet port (16), so that the sampling channel (13) is fully filled with the sample solution. The amount of sample solution that is needed for a measurement is determined by the sampling channel (13), and this sampling channel (13) is further defined by the thickness of the spacer layer (9).

EXAMPLE 2

In this example, all structures and procedures are the same with example 1, except polymer material is used for constituting the spacer. A thick layer of epoxy resin with the sample ditch (10) is disposed by the use of stainless stencil screen-printing technology on the insulating layer (6), and the epoxy resin is cured by the irradiation of UV light to form the spacer layer (9). Then, a composition of the bioactive formula is dropped on the surface of the reaction area (7) and dried at a temperature of 50° C. for 15 min to form a reagent layer (8). The protecting layer (11) coated with surfactant on the inner surface is adhered to the spacer layer (9) to form the inlet port (15) and outlet port (16).

EXAMPLE 3

In this example, all structures and procedures are the same with example 1, except polymer material is used for constituting the spacer. A thick layer of acrylic resin with the sample ditch (10) is disposed by the use of stainless stencil screen-printing technology on the insulating layer (9). Then, a composition of the bioactive formula is dropped on the surface of the reaction area (7) and dried at a temperature of 50° C. for 15 min to form the reagent layer (8). The protecting layer (11) coated with surfactant on the inner surface is adhered to the spacer layer (9) to form the inlet port (15) and the outlet port (16).

EXAMPLE 4

In this example, all structures and procedures are the same with example 1, except polymer material is used for constituting the spacer. A thick layer of polyester resin with the sample ditch (10) is disposed by the use of stainless stencil screen-printing technology on the insulating layer (9). Then, a composition of the bioactive formula is dropped on the surface of the reaction area (7) and dried at a temperature of 50° C. for 15 min to form the reagent layer (8). The protecting layer (11) coated with surfactant on the inner surface is adhered to the spacer layer (9) to form the inlet port (15) and the outlet port (16).

EXAMPLE 5

In this example, all structures and procedures are the same with example 1, except polymer material is used for constituting the spacer. A thick layer of silicone resin with the sample ditch (10) is disposed by the use of stainless stencil screen-printing technology on the insulating layer (9). Then, a composition of the bioactive formula is dropped on the surface of the reaction area (7) and dried at a temperature of 50° C. for 15 min to form the reagent layer (8). The protecting layer (11) coated with surfactant on the inner surface is adhered to the spacer layer (9) to form the inlet port (15) and the outlet port (16).

Although the invention has been explained in relation to its preferred embodiment, it is to be understood that many other possible modifications and variations can be made without departing from the spirit and scope of the invention as hereinafter claimed.

What is claimed is:

1. A biosensor comprising:
   a substrate (1) formed as a base of the biosensor;
   an anode conducting track (2) and a cathode conducting track (2') mounted on the substrate (1) to be a working electrode conducting track and a counter electrode conducting track respectively;
   a pair of electrode tracks (4,4') disclosed on the corresponding conducting track (2,2') to provide a suitable surface for electrochemical measurement of the biosensor;
   a switch comprising a switch pad (5) and a conducting pad (3), wherein the switch pad (5) is constructed on a conducting pad (3), and the switch controls actuation of the electrical system when the biosensor is inserted in a connector of a meter;
   an insulating layer (6) disposed on the electrode tracks (4,4') and the switch pad (5), and having an opening defined therein to construct a reaction area (7) and a connecting area (14);

a spacer layer (9) disposed on the insulating layer (6) and having a simple ditch (10) defined in the spacer layer (9) to correspond to the reaction area (7) and construct walls of the reaction area (7) to guide the sample solution flow;

a reagent layer (8) disposed on the reaction area (7) and re-dissolved rapidly when the reagent layer (8) contacts with the sample solution;

a protecting layer (11) having a hydrophilic membrane adhered on one face directed toward to the biosensor and traversely mounted on the sample ditch (10) of the spacer layer (9) to form an inlet port (15) and an outlet port (16) so that a sampling channel (13) is constructed inside the biosensor.

2. The biosensor as claimed in claim 1, wherein the substrate (10) is made of polymer materials selected from the following group comprising: polyvinyl chloride (PVC), polyethylene terephthalate (PET), polycarbonate (PC), polypropylene (PP), polyethylene (PE), polybutylene terephthalate (PBT), polystyrene (PVDF), polyamide (PA), bakelite, fiberglass, glass and ceramics.

3. The biosensor as claimed in claim 1, wherein the conducting tracks (2,2') and the conducting pad (3) are made of conductive materials selected from the following group comprising: carbon paste, silver paste, silver chloride paste, gold paste, palladium paste, gold platinum, and palladium.

4. The biosensor as claimed in claim 1, wherein the electrode tracks (4,4') and the switch pad (5) are made of materials selected form the following group: carbon paste, gold paste, palladium paste, gold, platinum, and palladium.

5. The biosensor as claimed in claim 1, wherein the insulating layer (6) is made of materials selected from the following group: acrylic resin, epoxy resin, polyurethane resin, silicon resin, phenol resin, alkyd resin, maleic alkyd resin, urea resin and polyester resin.

6. The biosensor as claimed in claim 1, wherein the insulating spacer layer (9) is made of materials selected from the following group: acrylic resin, epoxy resin, polyurethane resin, silicon resin, phenol resin, alkyd resin, maleic alkyd resin, urea resin, and polyester resin.

7. The biosensor as claimed in claim 1, wherein the reagent layer (8) is composed of an enzyme, a buffer solution, a carrier, an electrical media, and a surfactant.

8. The biosensor as claimed in claim 7, wherein the reagent (8) has a preferred composition comprising: Glucose oxidase, PVA, Potassium ferricyanide, Phosphate buffer, and Triton X-100.

9. The biosensor as claimed in claim 1, wherein material of the protecting layer is selected from polyvinyl chloride (PVC), polyethylene terephthalate (PET) and polypropylene (PP).

10. The biosensor as claimed in claim 1, wherein material of the hydrophilic membrane is selected form at least one of the following group: Triton X-100, polyoxymethylene sorbitan, starch, carboxymethyl cellulose, gelatin, acrylate, polyethylene glycol, polyvinyl alcohol, and polyvinylpyrolidone.

* * * * *